United States Patent [19]
Li

[11] Patent Number: 5,674,290
[45] Date of Patent: Oct. 7, 1997

[54] WATER-STABILIZED BIOPOLYMERIC IMPLANTS

[76] Inventor: Shu-Tung Li, 1 Kiowa Terrace, Oakland, N.J. 07436

[21] Appl. No.: 416,960

[22] Filed: Apr. 5, 1995

[51] Int. Cl.$^6$ ........................................................ A61F 2/02
[52] U.S. Cl. ........................... 623/11; 623/1; 530/356; 424/423; 424/424; 523/113
[58] Field of Search .................... 623/1, 11, 66, 623/901; 424/423, 424; 530/356; 523/113

[56] References Cited

U.S. PATENT DOCUMENTS

| | | | |
|---|---|---|---|
| 4,614,794 | 9/1986 | Easton et al. | 530/356 |
| 5,162,430 | 11/1992 | Rhee et al. | 525/54.1 |
| 5,308,889 | 5/1994 | Rhee et al. | 523/113 |
| 5,414,049 | 5/1995 | Sun et al. | 528/483 |
| 5,449,745 | 9/1995 | Sun et al. | 525/333.7 |

OTHER PUBLICATIONS

Bailey et al., "Irradiation–Induced Crosslinking of Collagen", Radiation Research 22:606–62, 1964.

Cheung et al., "The Effect of γ–Irradiation on Collagen Molecules, Isolated α–Chains, and Crosslinked Native Fibers", Journal of Biomedical Materials Research, 24:581–589, 1990.

Li et al., "Gamma–Irradiation of Reconstituted Collagen Matrices With Diffrent Water Contents: Implications in Implantable Device Devel.," The 20th Annual Meeting of the Society for Biomaterials, Apr. 5–9, 1994.

Liu et al, "The Effect of Gamma Irradiation on Injectable Human Amnion Collagen", Journal of Biomedical Research, 23:833–844, 1989.

Urry et al., "Irradiation Crosslinking of the Polytetrapeptide of Elastin and Compounding to Dacron to Produce a Potential Prosthetic . . . ", Journal of Biomedical Materials Research, 16:11–16, 1982.

Primary Examiner—John G. Weiss
Assistant Examiner—Francis K. Cuddihy
Attorney, Agent, or Firm—Fish & Richardson P.C.

[57] ABSTRACT

A method of treating a reconstituted biopolymeric implant which includes the steps of exposing the implant to an aqueous environment so that a final water content of the implant ranges from 5% by weight to a maximal water absorption capacity; and sealing the hydrated implant in a gamma ray-penetrable but bacteria- or virus-impenetrable material. Also disclosed is an implant preparation obtained by the above method.

16 Claims, No Drawings

WATER-STABILIZED BIOPOLYMERIC IMPLANTS

BACKGROUND OF THE INVENTION

This invention relates generally to sterilization of reconstituted biopolymeric implants.

Sterilization of medical implants has always been a critical issue facing medical implant manufacturers.

Sterilization by water steam (autoclave) is still the most common method for sterilizing hospital operating room instruments and clothes. The materials which are subjected to steam sterilization must be steam stable. Most surgical metal instruments fall into this category.

Sterilization by ethylene oxide gas is another common method for sterilizing medical products. Since the exposure of materials to ethylene oxide gas is under rather mild conditions, most medical implants can be successfully sterilized by this method. However, some residues of ethylene oxide remaining in the sterilized implant are known to be toxic. For example, ethylene chlorohydrin, a non-volatile toxic residue, is frequently produced and remains in the implant. Extensive evacuation does not reduce this residue to any significant degree. Ethylene chlorohydrin is particularly difficult to be removed from a reconstituted biopolymeric implant, which, as a porous matrix, has a large surface area for adsorption or absorption of this toxic residue.

An alternative to ethylene oxide sterilization is gamma irradiation or, less frequently, irradiation with electron beams. However, most polymeric materials including biopolymers are sensitive to gamma irradiation. The high energy gamma rays degrade the polymer chains by chain scission. The net result of gamma irradiation under most sterilization dose conditions is a reduction of molecular weight of the polymer. The gamma irradiation induced degradation can last for a long period of time by the entrapped free radicals produced within the polymeric material. The gamma irradiation of biologic materials under sterilization conditions, generally at a total dose of 25 kGy, produces materials that are partially degraded and therefore, are less stable. The stability of a biologic material may be defined by the thermal shrinkage temperature measurement of the irradiated polymer, the rate of degradation of a biopolymer by an enzyme, and by a measurement of the molecular weight.

The effect of gamma irradiation on biopolymeric polymer has been complicated by a number of factors. For example, it is known that gamma irradiation of collagen induces intermolecular crosslinking formation (which increases molecular weight, giving a structure stabilizing effect) as well as causes peptide bond scission (which reduces molecular weight, giving a structure destabilizing effect). The relative contribution of these effects depends on the microenvironment of the collagen and the dose of gamma ray to which the collagen is exposed.

SUMMARY OF THE INVENTION

An aspect of the present invention relates to a method of treating a reconstituted biopolymeric implant. The method includes the steps of (i) exposing the implant to an aqueous environment (e.g., a highly humid ambience, or a water bath) so that a final water content of the implant ranges from 5% (other acceptable values including 15%, 25% and 40%) by weight to a maximal water absorption capacity (i.e., fully hydrated); and (ii) sealing the hydrated implant in a gamma ray-penetrable but bacteria- or virus-impenetrable material (e.g., aluminum foil, plastics, foil/plastics composite, or glass). The sealed implant can then be irradiated with gamma rays.

Also within the scope of this invention is an implant preparation as obtained by the just-described method. That is, a reconstituted biopolymeric implant, which has a water content of 5% by weight or higher and is sealed in a gamma ray-penetrable but bacteria- or virus-impenetrable material. The implant thus sealed either is gamma ray-sterilized or remains to be sterilized by irradiation with gamma rays.

By "reconstituted biopolymeric implant" is meant an implant manufactured from polymers (e.g., via reorganization or chemical/physical modification of the polymers) which are known to be present in humans, animals and plants; particularly, from protein (such as elastin, collagen, and glycoproteins); polysaccharide (such as glycosaminoglycan, alginic acid, kitosan, and cellulose); or a mixture of protein and polysaccharide. While some of the above-mentioned biopolymers can be prepared by synthetic methods, reconstituted biopolymeric implants in general are derived from macromolecular components extracted from native tissues or organs. Polysaccharide- or protein-based reconstituted implants have been used in various medical applications. For example, a reconstituted collagen-based implant can be either used as a structural support to treat contour deformities of soft tissues. As another example, a reconstituted collagen-based implant can also be used as a delivery matrix in which a bioactive agent (e.g., a drug or cells) to be delivered is first dispersed before the implant is placed in the patient. Examples of reconstituted biopolymeric implants can be found in Chvapil, M., in "Biology of Collagen," Ed. Viidik, A., et al. 313–324, Academic Press, New York (1980); Chvapil, M., et al., Int. Rev. Connective Tissue Res. 6:1–56, Academic Press, New York, 1973; and Linhardt, R. J., et al. in "Biotechnology and Polymers," Ed. Charles, G. G. 155–166, Plenum Press, New York, (1991).

By "water content" is meant the amount of water contained in a reconstituted biopolymeric implant. More specifically, it is expressed as "% by weight" which is calculated from the formula: (weight of water/weight of a vacuum-dried implant)×100%. The "weight of a vacuum-dried implant" in the formula is obtained after the implant has been subjected to a vacuum-dry treatment, i.e., under a high vacuum condition (<150 μm Hg) for about 24 hours or an equivalent thereof, to remove all free water from the implant. The "weight of water" in the formula refers to the weight differential between a vacuum-dried implant and the hydrated form of the same implant.

The present invention teaches maintenance of a certain water content in a reconstituted biopolymeric implant during gamma irradiation, which enhances the structural stability of the implant.

Other features or advantages of the present invention will be apparent from the following detailed description of several embodiments, and also from the appending claims.

DETAILED DESCRIPTION OF THE INVENTION

One method of obtaining a reconstituted biopolymeric implant with a predetermined water content prior to its gamma sterilization is vacuum-drying the implant, followed by exposure of the dried implant to a high humidity environment (e.g., humidity greater than 90%) at a temperature not higher than the temperature that will effect the structure of the biological material (generally, less than 40° C.) for a period of time. As a result, the implant absorbs a sufficient amount of water moisture. A high humidity environment can be generated from water vapor at a defined temperature where the implant is exposed to, or by passing steam to a chamber within a defined temperature range. In general, a reconstituted porous biopolymeric implant will absorb a water content ranging from 40% to 70% by weight at a relative humidity of greater than 95% for about 24 hours. Alternatively, the vacuum-dried implant can be soaked in an aqueous solution such that it is fully hydrated (i.e., has a water content which is equal to its maximal water absorption capacity). The water content of a porous implant after soaking will generally be in the range of from 100% to 500% by weight.

A high water content can be obtained for an implant if the implant is highly porous and provides more interstitial space for the retention of water. For a highly porous collagen-based implant with a density of 0.05 g collagen per $cm^3$ volume matrix, the fully hydrated implant will generally have a water content of 500% to 1,000% by weight. Even a higher water content may be obtained by further reducing the density of the implant.

If necessary, one can mechanically compress, or partially dry, an implant which has been overly hydrated in an aqueous environment in order to effect a desired water content.

It is preferred that the hydrated implant be sealed in a moisture- or water-proof package (e.g., in a glass bottle) such that the water content does not vary significantly during radiation sterilization. Of note, a fully hydrated implant can undergo gamma irradiation with an excess of water which is not absorbed by the implant.

The total dose of gamma ray for sterilizing a reconstituted biopolymeric implant is generally in the range from about 15 kGy to about 35 kGy, depending on the bioburden level (initial contamination) of the implant. For example, according to the American Association of Medical Instrumentation, a bioburden level of 3 colonies per implant requires a total dose of 16.5 kGy to obtain a sterilization assurance level of $10^{-6}$ (i.e., the probability of being non-sterile).

Without further elaboration, it is believed that a person of ordinary skill in the art can, based on the description set forth above, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Preparation of a collagen-based implant

The fat and fascia of the bovine flexor tendon were carefully cleaned and removed and washed with water. The cleaned tendon was frozen and diminuted by slicing into 0.5 mm slices with a meat slicer. The tendon was first defatted with isopropanol (tendon:isopropanol=1:5 v:v) for 8 hours at 25° C. under constant agitation. The extraction solution was discarded and equal volume of isopropanol was added and the tendon slices was extracted again overnight at 25° C. under agitation. The tendon was then extensively washed with deionized, distilled water to remove the residual isopropanol. The defatted tendon was then extracted with 10 volumes of 1M NaCl for 24 hours at 4° C. under agitation.

The salt extracted tendon was washed with deionized, distilled water. The fibers were next extracted with 10 volumes of 1.0M NaOH for 24 hours at 25° C. in the presence of 1M $Na_2SO_4$ under constant agitation. The alkaline extracted collagen was then collected by filtration and neutralized with 0.1M HCl and the fibers collected, washed to remove the residual salt and frozen.

An aliquot of the above purified fibers was first suspended in a 0.07M lactic acid solution. The amount of fibers and the acid solution used was such that a 0.7% (w/v) of collagen dispersion was reached. The swollen fibers were then homogenized in a Silverson Homogenizer. The dispersed collagen material thus obtained was filtered through a 40 µm stainless steel mesh before it was ready for the implant fabrication.

A 500 ml of collagen dispersion was neutralized with 0.5% $NH_4OH$ to the isoelectric point (about pH 5) to coacervate the fibers. The coacervated fibers were partially dehydrated and molded into a circular mold and further dehydrated in the mold to obtain a matrix of a predetermined density.

The molded matrix was frozen and then subjected to a freeze-drying procedure in a Virtis freeze dryer (Virtis Company Inc., Gardiner, N.Y.). The conditions for freeze-drying are: freeze at –40° C. for 6 hours, drying at 150 µm Hg at –10° C. for 48 hours followed by drying at 25° C. for 24 hours. The freeze-dried collagen matrices were then subjected to chemical crosslinking using formaldehyde to stabilize the matrix. The crosslinking procedure was conducted in a crosslinking chamber containing formaldehyde vapor (generated by a 2% formaldehyde solution at 25° C.) with 95% relative humidity (water vapor) at 25° C. for 24 hours. The implant contained approximately about 40%–60% by weight after the crosslinking step. The implant thus obtained, after washing in a water bath, was first air dried and then vacuum dried before adjustment of water contents.

Preparation of a collagen implant for gamma sterilization

The dried implant was humidified in a humidifying chamber at a relative humidity of >95%. The overall water content in the implant was obtained by weighing the implant before and after the humidification procedure.

For a water content of greater than 100% by weight, the implant was first soaked in water, followed by removal of excess water via mechanical compression and partial drying in air. A fully hydrated implant (the maximal amount of water an implant could absorb) had a water content of about 400% by weight. A water content of less than 100% by weight was obtained by equilibrating the implant with a saturated water vapor for a variable period of time, generally from about 8 to about 48 hours, and at a temperature of from about 20° C. to about 30° C.

The humidified implant was packaged into a moisture-proof foil package (the foil packaging material was obtained from: Technipaq, Inc. Crystal Lake, Ill.) and then heat-sealed. The packaged implant was sterilized by gamma ray irradiation at a total dose level of 17.5 kGy to 18.3 kGy (Isomedix Inc., Whippany, N.J.).

Characterization of gamma-sterilized collagen implants

Two structural parameters were characterized: hydrothermal shrinkage temperature (Ts) and enzyme digestion, two parameters which reflect the stability of the polymeric chains and the intermolecular interactions in a reconstituted biopolymeric implant.

(a) Hydrothermal shrinkage temperature

The Ts values of collagen implants which had undergone gamma sterilization with various water contents (0%, 20%, 40%, 125%, 200%, and 400% by weight) were determined as follows:

A strip of each sterilized collagen implant was equilibrated in a phosphate buffered saline, pH 7.4 for 10 minutes at room temperature. The temperature of the solution was increased at a rate of 1° C. per minute. The length of the implant was continuously monitored. The Ts value was defined as the temperature at which the length of the implant started to change.

The results of this hydrothermal shrinkage study are summarized in the table below:

| Hydrothermal Shrinkage of Implants Post Gamma-Irradiation | |
|---|---|
| Water Content (% by weight) | Shrinkage Temperature (°C.) ± Std. Dev. |
| 0 | 56.0 ± 2.6 |
| 20 | 64.7 ± 0.9 |
| 40 | 68.4 ± 0.6 |
| 125 | 66.6 ± 1.2 |
| 200 | 67.1 ± 0.7 |
| 400 | 65.2 ± 0.3 |
| Control* | 72.3 ± 1.2 |

*not subjected to gamma irradiation

As shown in the above table, the shrinkage temperatures of the gamma-sterilized hydrated implants were lowered by 3.9° C. (water content 40% by weight) to 7.6° C. (water content 20% by weight) as compared to that of the non-gamma treated implant. By contrast, the shrinkage temperature of the vacuum-dried implant (water content 0% by weight) was lowered by as much as 16.3° C.

(b) Trypsin digestion

Strips of the implants were incubated in 5 ml of trypsin solution (2,000 units/ml, 0.46M Tris, 0.023M $CaCl_2$, pH 8.0) at 37° C. for various lengths of time. Aliquots of the supernatants were sampled at different time points and assayed for the hydroxyproline content. The hydroxyproline contents were converted to the collagen contents. The results of this study are summarized in the table below:

| Trypsin Digestion of Implants Post Gamma-Irradiation | | | |
|---|---|---|---|
| Water Content | % Collagen Digested by Trypsin | | |
| (% by weight) | 2 days | 5 days | 7 days |
| 0 | 19.6 ± 2.2 | 34.7 ± 0.6 | 49.1 ± 4.0 |
| 40 | 3.0 ± 0.6 | 10.6 ± 1.8 | 14.5 ± 2.5 |
| 125 | 3.74 ± 0.3 | 11.3 ± 0.5 | 15.23 ± 2.4 |
| Control* | 2.48 ± 0.5 | 8.8 ± 0.7 | 12.5 ± 0.5 |

*not subjected to gamma irradiation

As shown in the above table, the two implants with respective water contents of 40% and 125% by weight were only slightly more susceptible to trypsin digestion than the non-radiated implant. By contrast, the implant irradiated in the dry state was digested at a significantly higher rate.

EXAMPLE 2

Preparation and sterilization of polysaccharide implants

Five grams of alginic acid (Sigma Chemical Co., St. Louis, Mo.) are dissolved in 500 ml of distilled water in the presence of 0.001M ethylene diamine tetraacetic acid to chelate any metal ions. The solubilized alginic acid is filtered through a 200 mesh stainless steel filter to eliminate the undissolved particles and contaminants.

Calcium ions in the form of 0.1M $CaCl_2$ solution is slowly added to the alginic acid solution to precipitate the alginic acid from the solution. The precipitated fibers are removed from the solution by filtration through a 40 mesh stainless steel filter.

The alginic acid fibers are then partially dehydrated and molded into a circular mold and further dehydrated in the mold to obtain a polysaccharide matrix of pre-determined density.

The alginic acid fibers are then subjected to freeze-drying, adjustment of water contents, packaging, and gamma-irradiation in manners identical or analogous to those described in Example 1.

EXAMPLE 3

Preparation and sterilization of collagen implants containing glycosaminoglycan

A dispersed collagen material which has been filtered through a 40 µm stainless steel mesh is obtained following a procedure identical to that described in Example 1.

To a 500 ml of the collagen dispersion thus obtained, 0.1 g hyaluronic acid (LifeCore, Chaska, Minn.) and 0.1 g chondroitin sulfate (Seikagaku Corporation, Tokyo, Japan) were added and uniformly mixed with the dispersion. Subsequent coacervation, molding, freeze-drying, crosslinking, adjustment of water contents, packaging, and gamma-irradiation are performed in manners identical or analogous to those described in Example 1.

EXAMPLE 4

Preparation of implants containing a bioactive agent

A dispersed collagen material which has been filtered through a 40 µm stainless steel mesh is obtained following the identical described in Example 1.

To a 200 ml of the collagen material thus obtained, a 0.01 g epidermal growth factor (Sigma Chemical Co., St. Louis, Mo.) is slowly added with constant mixing for uniform dispersion. Subsequent coacervation, molding, freeze-drying, crosslinking, adjustment of water contents, packaging, and gamma-irradiation are performed in manners identical or analogous to those described in Example 1.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the appending claims.

For example, while the gamma ray limitation is included in all of the appending claims, both treatment of a hydrated implant for irradiation with electron beams and an implant preparation obtained from such treatment are indeed contemplated embodiments of this invention under the doctrine of equivalents.

What is claimed is:

1. An implant preparation comprising:
   a reconstituted biopolymeric implant which has a water content ranging from 5% by weight to a maximal water absorption capacity; and
   a gamma ray-penetrable but bacteria- or virus-impenetrable material;
   wherein said implant is sealed in said material.

2. The implant preparation of claim 1, wherein said water content ranges from 15% by weight to a maximal water absorption capacity.

3. The implant preparation of claim 2, wherein said water content ranges from 25% by weight to a maximal water absorption capacity.

4. The implant preparation of claim 3, wherein said water content ranges from 40% by weight to a maximal water absorption capacity.

5. The implant preparation of claim 1, wherein said implant is a polysaccharide-based implant.

6. The implant preparation of claim 5, wherein said water content ranges from 15% by weight to a maximal water absorption capacity.

7. The implant preparation of claim 6, wherein said water content ranges from 25% by weight to a maximal water absorption capacity.

8. The implant preparation of claim 7, wherein said water content ranges from 40% by weight to a maximal water absorption capacity.

9. The implant preparation of claim 1, wherein said implant is a protein-based implant.

10. The implant preparation of claim 9, wherein said water content ranges from 15% by weight to a maximal water absorption capacity.

11. The implant preparation of claim 10, wherein said water content ranges from 25% by weight to a maximal water absorption capacity.

12. The implant preparation of claim 11, wherein said water content ranges from 40% by weight to a maximal water absorption capacity.

13. The implant preparation of claim 1, wherein said implant is a collagen-based implant.

14. The implant preparation of claim 13, wherein said water content ranges from 15% by weight to a maximal water absorption capacity.

15. The implant preparation of claim 14, wherein said water content ranges from 25% by weight to a maximal water absorption capacity.

16. The implant preparation of claim 15, wherein said water content ranges from 40% by weight to a maximal water absorption capacity.

* * * * *